United States Patent [19]

Sato

[11] Patent Number: 4,996,755
[45] Date of Patent: Mar. 5, 1991

[54] CLIP DRIVER

[76] Inventor: Hisao Sato, Daini-Hikariso, 10, Toyotamaminami 3-Chome, Nerima-Ku, Tokyo, Japan

[21] Appl. No.: 474,328

[22] Filed: Feb. 2, 1990

[30] Foreign Application Priority Data

May 31, 1989 [JP] Japan .............................. 1-63465[U]

[51] Int. Cl.⁵ .............................................. A61B 17/00
[52] U.S. Cl. .................................................. 29/243.56
[58] Field of Search ................... 29/243.56, 270, 278, 29/814; 227/19, DIG. 1; 128/334

[56] References Cited

U.S. PATENT DOCUMENTS

| 4,332,060 | 6/1982 | Sato . | |
|---|---|---|---|
| 4,353,157 | 10/1982 | Sato . | |
| 4,637,395 | 1/1987 | Caspar et al. | 29/243.56 |
| 4,791,707 | 12/1988 | Tucker | 29/243.56 |
| 4,854,317 | 8/1989 | Braun | 29/243.56 |

Primary Examiner—Robert C. Watson
Attorney, Agent, or Firm—Kanesaka and Takeuchi

[57] ABSTRACT

Disclosed is a clip driver for binding documents or the like together by using a clip which is formed from a single elastic plate-like member and which is constituted by a bent portion and a pair of grasping portions continued from the bent portion, the grasping portions having extremities normally contacting with each other so as to grasp the documents or the like between the grasping portions. The clip driver comprises: a lower casing having an upper surface for mounting thereon a plurality of the clips; an upper casing fitted with the lower casing and having a clip insertion inlet formed at a rear end thereof for insertion of the clips; a knob for driving out the clip, the knob being longitudinally slidably and vertically movably mounted in a rectangular opening formed in the upper casing at a front end side thereof; and clip opening spring members provided in an insertion inlet formed between the lower and upper casings for opening the grasping portions of the clip in the directions opposite to each other. The knob is normally biased by an elastic member to a position at a rear end side of the clip driver and, at the same time, biased so that a push-out portion of the knob comes to a lifted position to thereby allow the clip to pass by the push-out portion thereunder.

7 Claims, 2 Drawing Sheets

CLIP DRIVER

BACKGROUND OF THE INVENTION

1. Field of the Invention

The present invention generally relates to a clip driver for binding documents or the like by using a clip, and particularly relates to a clip driver in which a plurality of clips each formed of a single elastic plate-like member which is bent to have a pair of grasping portions abutting against each other is accommodated in the clip driver and successively sent to a position in which the grasping portions of the clip are opened so as to grasp documents or the like therebetween.

2. Description of the Prior Art

To bind a plurality of loose documents together, generally, a stapler, a Gem clip, or the like has been used. In a stapler, however, there has been a disadvantage in that the documents are injured because a staple accommodated in the stapler is stuck through the documents to bind them together. In the case of a Gem clip in which documents are inserted between double ring portions of the Gem clip so as to be bound together, on the other hand, there is a disadvantage in that the documents are apt to come off from the Gem clip and that the Gem clip is not suitable to clip a large number of documents together, although the Gem clip has an advantage in that the documents are not injured by the Gem clip. There has been therefore proposed a clip which is formed in such a manner that an elastic plate-like member is bent to form a pair of grasping portions abutting against each other at the extremities thereof and rotatable levers are provided outside the grasping portions so that the levers are operated by fingers to thereby open the nip between the grasping portions so as to grasp documents or the like therebetween. In the clip, however, there has been a disadvantage in that in order to bind a large number of documents together, the clip must be made large in size and the levers must be pushed with strong force to move the abutment surfaces away from each other. Such a clip is therefore unsuitable for a person whose finger force is weak. Further, the opposite side edges of the elastic plate member are arcuately outward curved so as to rotatably support the levers, and therefore if other documents are stacked on the documents bound already by this clip, there has been a possibility that the other documents stacked on the documents bound already by such a clip may be injured by the curved portions of the clip.

In U.S. Pat. No. 4,332,060 patented Jun. 1, 1982, therefore, the inventer of this application has proposed a clip having no such levers as described above and also disclosed a driver for driving out such a clip. That is, the inventor of this application has proposed a spring clip which is formed by bending a single elastic plate-like member so as to have a bent portion and a pair of grasping portions continued to the bent portion, the grasping portions being normally in contact with each other. The spring clip is made to grasp documents or the like by use of a clip driver which is constituted by a clip accommodation portion for accommodating the spring clip therein, a clip opening portion provided at the front end of the accommodation portion and arranged so that the clip opening portion may be inserted into a space between the grasping portions of the clip so as to open the grasping portions against the elasticity of the clip, and a lever slidably inserted into the accommodation portion from the rear end thereof so as to abut against the bent portion of the clip to thereby push the clip toward the clip opening portion. That is, the clip opening portion includes a guide spring which urges the grasping portions of the clip to open the nip therebetween when the clip opening portion is inserted into the nip between the grasping portions. If the lever is further pushed after the nip between the grasping portions have been opened by the guide spring and documents or the like have been inserted between the grasping portions, the clip is ejected out of the front end of the clip driver under the condition that the documents are grasped by the clip.

In such a clip driver, however, there has been a disadvantage in that since only one clip is pushed out by the front end of the lever, it is impossible to accommodate a plurality of clips in advance so as to successively push out the accommodated clips. Accordingly, inconveniently, it has been necessary to load a clip into the accommodation portion every time a clip is to be driven out.

Accordingly, the inventor of this application have improved the aforementioned clip driver, and have proposed, in U.S. Pat. No. 4,353,157 patented Oct. 12, 1982, a hand clip driver in which a knob is slidably provided above an accommodation portion so that a clip in the accommodation portion can be pushed out to a clip opening portion by means of the knob, and in which a plurality of clips can be loaded in the accommodation portion so that after one clip at the head of the loaded clips has been pushed out the knob is retreated to abut on a bent portion of the next clip and then pushed forward to displace this clip to the clip opening portion.

This hand clip driver has an advantage in that a plurality of clips can be accommodated in the clip driver in advance so that documents or the like can be bound together successively and continuously. This hand clip driver, on the other hand, has a disadvantage in that it is necessary to retreat the knob in order to send a new clip to the clip opening portion each time. Thus, the operation is troublesome. Further, the clip driver is so complicated in structure that the parts are large in number and the cost of the clip driver is high.

SUMMARY OF THE INVENTION

It is therefore an object of the present invention to provide a clip driver having a simple configuration in which a new clip can be located at a clip opening portion without operating a knob.

It is another object of the present invention to provide a clip driver in which parts are reduced in number and the clip driver can be assembled easily.

In order to attain the above objects, according to an aspect of the present invention, the clip driver for binding documents or the like together uses a clip formed from a single elastic plate-like member and constituted by a bent portion and a pair of grasping portions continued from the bent portion, the grasping portions having extremities normally contacting with each other so as to grasp the documents or the like between the grasping portions. The clip driver comprises: a lower casing having at its front end a lower opening portion forming a part of an insertion inlet for the documents or the like, the lower casing having an upper surface on which at least one clip is mounted with the grasping portions directed toward the insertion inlet so that the clip is slidable in a longitudinal direction of the clip driver; an upper casing having at its front end an upper opening portion forming the insertion inlet together with the lower opening portion of the lower casing and having at its rear end a clip insertion inlet for inserting the clip; a knob mounted in a rectangular opening which is formed in the upper casing at its front end side so as to extend in the longitudinal direction, the knob being slidable in the longitudinal direction and being movable up and down within a predetermined range, the knob having a knob projection portion projected upward from the opening, a push-out portion formed on a front end of the knob projection portion so that the push-out portion comes to abut on the bent portion of the clip when the knob is lowered, and a projection portion rearward extending from a rear end of the knob projection portion; clip opening spring members provided in the insertion inlet formed by the lower and upper casings for opening the grasping portions of the clip in the directions opposite to each other; and an elastic member provided with its opposite ends attached to the projection portion and to a lower surface portion of the upper casing so that the knob is normally biased toward a rear end of the clip driver and at the same time the push-out portion is biased upward.

Preferably, in the clip driver according the present invention, a substantially horizontally-projected projection portion is formed on a rear end surface of the lower casing and an engagement portion to be engaged with the projection portion is formed on a rear end portion of the upper casing so that the lower and upper casings are assembled in the condition that the engagement portion engages with the projection portion, the assembly of the lower and upper casings being fixed at a periphery thereof at the insertion inlet side by means of a fastening band.

Thus, in the clip driver according to the present invention, since the front end of the knob for pushing-out the clip is normally biased upward by the elastic member, if the knob is released from a finger after the clip at the head of the loaded clips has been pushed out of the clip driver, the next clip can be made positioned in front of the knob without any obstacle by the front end of the knob. Consequently, unlike the conventional clip driver, it is not necessary to retreat the knob to make the next clip position in front of the knob. Further, the clip driver according to the present invention is constituted mainly by three members, that is, the lower casing, the upper casing, and the knob, and each of the members has a simple structure. Each member can be therefore integrally formed through injection molding or the like, and the members can be easily assembled. Accordingly, the clip driver can be provided at a low cost.

These and other object and advantages of the present invention will become clear by the following description of a preferred embodiment of the present invention.

DETAILED DESCRIPTION OF THE PREFERRED EMBODIMENT

Figure 1:
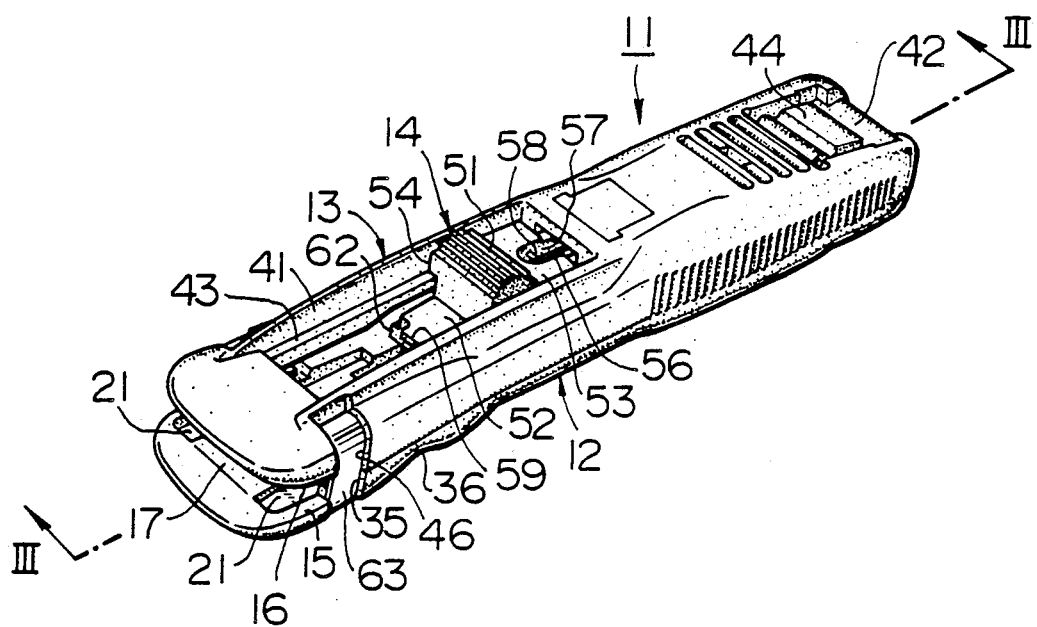
FIG. 1 is a perspective view showing an embodiment of the clip driver according to the present invention.

A preferred embodiment of the clip driver according to the present invention will be described with reference to the accompanying drawings hereunder. In the following description, the terms "front" and "rear" are defined to be the sides of the clip drive in which a clip is driven out of and inserted into the clip driver, respectively. The clip driver 11 is constituted mainly by a rectangular lower casing 12, and an upper casing 13 attached on the lower casing 12 so as to cover the lower casing 12, and a knob 14 attached on the upper casing 13 slidably in the longitudinal direction of the upper casing 13. All the lower casing 12, the upper casing 13, and the knob 14 are formed of synthetic resin. A lower inclination rim 15 is formed on the periphery of a front end portion of the lower casing 12 so as to be upward obliquely inclined toward a rear end portion of the lower casing 12, and, on the other hand, an upper inclination rim 16 is formed on the periphery of a front end portion of the upper casing 13 so as to be downward obliquely inclined toward a rear end portion of the upper casing 13. When the lower and upper casings 12 and 13 have been assembled, the lower and upper inclination rims 15 and 16 form an insertion inlet 17 at the front end of the assembly of the lower and upper casings 12 and 13 so that documents or the like to be bound together are inserted thereinto.

Figure 2:
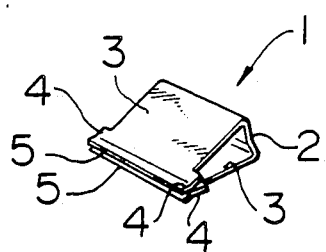
FIG. 2 is a perspective view showing a clip to be used in this embodiment.

A clip 1 to be used in the clip driver 11 is constituted by an integrally continuous body which is formed by bending a rectangular plate-like member of metal or synthetic resin in a manner so that, as shown in detail in FIG. 2, a bent portion 2 is provided at the longitudinally central portion of the plate-like member and two grasping portions 3 having extremities elastically contacting with each other are provided integrally with the bent portion. A pair of sideward projecting lug portions 4 for opening or widening the nip between the grasping portions 3 are formed on the front end opposite sides of each of the grasping portions 3, that is, a pair of upper and lower sideward projecting lug portions 4 are formed at each of the front end opposite sides of the clip 1. Guide portions 5 bent in the outward directions opposite to each other are formed on the respective extremities of the grasping portions 3 including the lug portions 4 so that the grasping portions 3 can be easily opened. The lower casing 12 of the clip driver 11 is provided with clip opening spring members 21 attached to the lower casing 12 at the widthwise opposite sides of the longitudinal front end portion thereof where the insertion inlet 17 is formed. Those clip opening spring members 21 are provided so as to be inserted into a space between the corresponding pair of upper and lower lug portions 4 to open the space, when the clip 1 is positioned in this front end portion. Each of the clip opening spring members 21 has a substantially lateral-turned V-shape in cross section and has an insertion hole 22 formed in the vicinity of the vertex of the V-shape thereof. The clip opening spring members 21 are pressed so that the insertion holes 22 thereof are fitted onto corresponding upstanding pins 23 formed on the lower casing 12 integrally therewith so that the clip opening spring members 21 are attached to the lower casing 12. The positions of the insertion holes 22 and pins 23 are selected so that the respective inner side edges of the clip opening spring members 21 never come into contact with the bent portion 2 of the clip 1 while they can be inserted into the respective spaces between the upper and lower lug portions 4 of the clip 1. The lower casing 12 has a longitudinally extending groove 24 formed therein. The width of the groove 24 is selected so as to be substantially equal to the distance between the respective outer edges of the lug portions 4 at the widthwise opposite sides of the clip 1 so that the clip 1 can be inserted into the groove 24. A recess 25 lowered in level than the groove 24 is formed in a front end portion of the groove 24 in the lower casing 12. A front end groove 26 which is deeper than the groove 24 but shallower than the recess 25 is formed also in the lower casing 12 so as to extend from the substantially central portion of the recess 25 toward the front end of the casing 12. A pair of lug guide step portions 28 for holding thereon the lug portions 4 at the widthwise opposite sides of the clip 1 are formed on widthwise opposite side walls 27 of the groove 24 at the inside lower portions thereof so as to longitudinally extend to the vicinity of the vertexes of the clip opening spring members 21 respectively. Further, the lower casing 12 is provided, at its rear end portion, with a pair of guide projections 29 inclined downward from the rear end portion of the lower casing 12 toward the front end of the same so as to be continued to the lug guide step portions 28 respectively. The rear end portions of the respective guide projections 29 are connected to each other through a horizontally extending connection portion 31. A pair of fitting rims 32 is formed on the respective upper surfaces of the pair of side walls 27 so as to make the lower casing 12 fit into the upper casing 13, and a pair of upstanding pins 33 is formed in the vicinity of the pins 23 so as to fit into fitting holes (not shown) formed in the upper casing 13. The front end portions of the lug guide step portions 28 positioned under the clip opening spring members 21 have engagement step portions 34 having upper surface portions lower than the lug guide step portions 28 respectively. The opposite side edges of the respective clip opening spring members 21 are partly disposed on the engagement step portions 34. A widthwise elongated groove 35 is formed in the outer periphery of the lower casing 12 at a portion corresponding to the clip opening spring members 21. A recess portion 36 is formed in the outside lower surface of the bottom of the lower casing 12 at a portion between the groove 35 and a position corresponding to the recess 25 so that an operator may put his/her forefinger in the recess portion 36 in use of the clip driver 11. A pair of spring sockets 37 are formed in the lower casing 12 at the front end opposite side portions thereof surrounded by the lower inclination rim 15 so that the front ends of the one leg portions of the clip opening spring members 21 are removably accommodated in the spring sockets 37 respectively.

Figure 3:
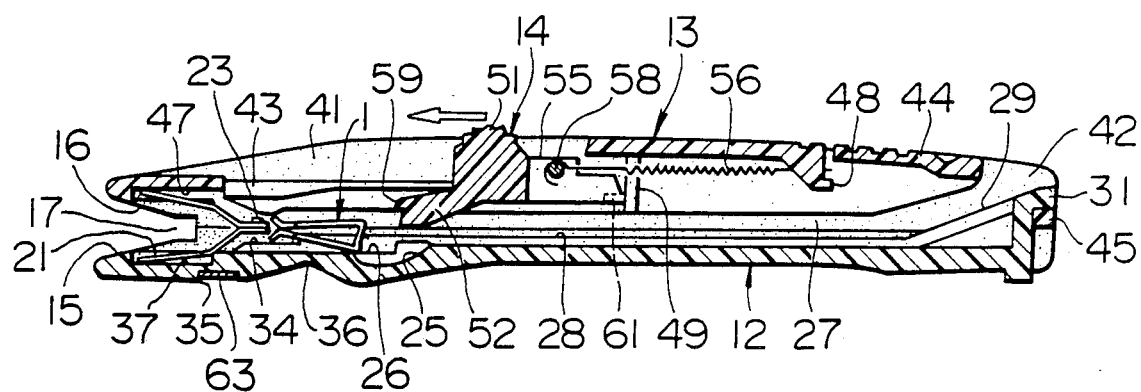
FIG. 3 is a longitudinal side section view of the clip driver taken along line III—III in FIG. 1, wherein the knob has been displaced to the front end.
Figure 4:
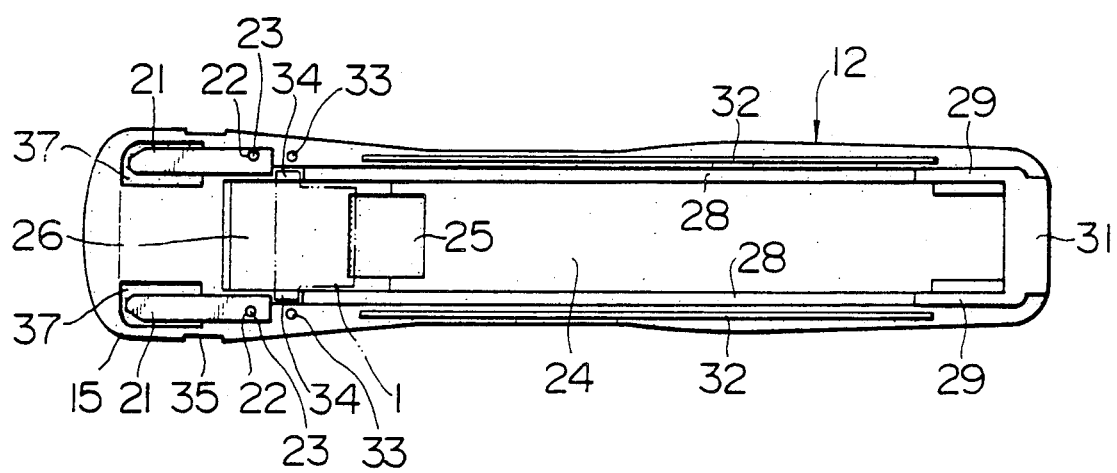
FIG. 4 is a plan view showing only the lower casing of FIG. 1.

The upper casing 13 generally having an inverted elongated dish shape is provided with a rectangular opening 41 formed therethrough so as to extend from the substantially longitudinally central portion toward the front end thereof and a clip insertion inlet 42 formed at the rear end thereof as shown in FIGS. 1 and 3. A pair of horizontally extending guide rims 43 are formed on the widthwise opposite inner side surfaces of the opening 41. A cover portion 44 for preventing an inserted clip 1 from coming off is formed at the clip insertion inlet 42 so as to extend from the front end of the clip insertion inlet toward the rear end of the same. The cover portion 44 is made to have elasticity so that the cover portion may be elastically vertically biased. The gap between the rear or free end of the cover portion 44 and the connection portion 31 of the lower casing 12 is selected so as to be a little narrower than the thickness of the bent portion 2 of the clip 1. A step portion 45 is formed on the rear end portion of the upper casing 13 so that the step portion 45 may abut on the lower surface of the connection portion 31 of the lower casing 12. Grooves 46 are formed in the front end portion of the upper casing 13 at its widthwise opposite sides so that the grooves 46 communicate with the groove 35 when the upper casing 13 is fitted into the lower casing 12. The respective front ends of the guide rims 43 extend to the vicinity of the respective vertexes of the clip opening spring members 21, and spring sockets 47 for removably accommodating the respective other leg portion of the front ends of the clip opening spring members 21 are formed at portions between the front ends of the guide rims 43 and the upper inclination rims 16.

The knob 14 is slidably inserted into the opening 41 of the upper casing 13 as shown in FIGS. 1 and 3. The knob 14 is constituted by integrally formed three portions, that is, a knob projection portion 51 with its top end end projected upward from the opening 41, a push-out portion 52 frontward-downward projected from the knob projection portion 51 for abutting, at its front end, against the bent portion 2 of the clip 1 disposed at the head of the inserted clips, and a horizontal portion 53 substantially horizontally rearward extending from the rear end of the knob projection portion 51. The respective lower portions of the knob projection portion 51 and horizontal portion 53 and the push-out portion 52 are positioned between the guide rims 43. Opposite side portions 54 of the knob projection portion 51 extend so that the lower end surfaces of the opposite side portions 54 are respectively located above the upper surfaces of the respective guide rims 43 with a predetermined gap therebetween. The horizontal portion 53 is provided, at its knob projection portion 51 side, with extending portions 55 so that the lower end surfaces of the extending portions 55 are respectively located above the upper surfaces of the guide rims 43 with a predetermined gap therebetween. A spring 56 is situated between the rear end of the upper casing 13 and the horizontal portion 53 so that the knob 14 is always pulled elastically rearward by the spring 56. Specifically, a notched portion 57 extending in the sliding direction of the knob 14 is formed substantially at the widthwise central portion in the rear portion of the horizontal portion 53 so that the opened end of the notched portion 57 is located at the rear end portion of the horizontal portion 53 and an engagement member 58 is formed in the notched portion 57. An engagement projection 48 is formed on the lower surface of the rear end portion of the upper casing 13 so as to project rearward, the spring 56 being hung, at its opposite ends, to the engagement member 58 and the engagement projection 48 respectively. An engagement portion 59 is formed integrally with the push-out portion 52 on the front end upper surface thereof so as to project a little from the front end edge of the push-out portion 52 so that the engagement portion may engage with the upper shoulder portion of the bent portion 2 of the clip 1.

The horizontal portion 53 of the knob 14 has a pair of rear horizontal projections 61 formed at rear opposite sides thereof so as to horizontally sideward extend toward the opposite side surfaces of the opening 41 to thereby engage with the lower surfaces of the guide rims 43 respectively. On the other hand, the push-out portion 52 has front horizontal projections 62 formed at the front end upper surface thereof so as to extend horizontally sideward so that the front horizontal projections 62 engage with the lower surfaces of the guide rims 43 respectively. Thus, the knob 14 is disposed so as to be retained in the guide rims 43 between the respective lower surfaces of the side portions 54 of the knob projection portion 51 and the respective upper surfaces of the rear and front horizontal projections 61 and 62 so that the knob 14 may be slidably moved without coming off from the opening 41.

The rearward displacement of the knob 14 by the spring 56 is limited by abutment of the rear end edge of the horizontal portion 53 against a limit projection 49 integrally formed on the rear side lower surface of the upper casing 13. The rear end edge portion of the horizontal portion 53 which may abut against the limit projection 49 is lower than the engagement projection 48 and tapered so that the lower end edge of the rear end edge portion is more projected rearward than the upper end edge of the same. Thus, although elastic force is applied onto the knob 14 by the spring 56 so as to rotate the knob 14 clockwise about the rear end edge of the horizontal portion 53 in FIG. 3, the rotation force of the knob 14 is limited because the front horizontal projections 62 of the push-out portion 52 engage with the lower surfaces of the guide rims 43 respectively, so that the knob 14 is substantially horizontally elastically supported. The length of the front end portion of the push-out portion 52 is selected so that the front end portion of the push-out portion 52 is positioned substantially at the rear end portion of the recess 25 when the rear end edge of the horizontal portion 53 engages with the limit projection 49.

The lower and upper casings 12 and 13 are fixed to each other by fitting a fastening band 63 formed of springy metal and having a substantial C shape into the grooves 35 and 46 formed in the outer peripheries of the lower and upper casings 12 and 13 respectively.

Assembling of the clip driver 11 will be described. First, the knob 14 is fitted into the opening 41 of the upper casing 13. This operation of insertion is performed as follows. The knob 14 is oriented substantially at right angles relative to the longitudinal direction of the opening 41 and then the front end of the push-out portion 52 is inserted into the opening 41 at the front end thereof. Then, the knob 14 is turned so that the horizontal portion 53 is located above the opening 41 while making the front horizontal projections 62 of the push-out portion 52 positioned under the lower surfaces of the guide rims 43 respectively. As a result, the front horizontal projections 62 of the push-out portion 52 are located under the lower surfaces of the guide rims 43 respectively, and the rear horizontal projections 61 of the horizontal portion 53 are located on the upper surfaces of the guide rims 43 respectively. Since the rear horizontal projections 61 are formed on the rear end side surfaces of the notched portion 57, the opposite-side portions of the notched portion 57 are made elastic. Accordingly, if these opposite-side portions are pushed toward the notched portion 57, the horizontal portion 53 can be easily inserted into the opening 41. Next, one and the other ends of the spring 56 are hung to the engagement member 58 and the engagement projection 48 respectively.

The clip opening spring members 21 are attached onto the lower casing 12 by fitting the insertion holes 22 onto the two pins 23 so that the respective openings of the clip opening spring members 21 are directed to the front end of the lower casing 12 and that the clip opening spring members 21 are arranged parallel to each other. Next, the lower casing 12 is covered with the upper casing 13 while making the rear end portion 45 of the upper casing 13 abut on the lower surface of the connection portion 31 of the lower casing 12. If grooves are formed in lower end opposite side surfaces of the upper casing 13 so that the fitting rims 32 of the lower casing 12 may be fitted into the grooves, the casings 12 and 13 can be assembled without slipping. Further, the pins 23 and 33 are fitted into holes which are formed in the upper casing 13. As a result, a path for the clip 1 is formed in the inside of the lower and upper casings 12 and 13. Finally, the fastening band 63 is fitted into the grooves 35 and 46 to thereby complete the assembling of the clip driver 11. Although the two pins 23 and 33 are provided in this embodiment, only one pin 23 may be sufficient.

Thus, the clip driver 11 is constituted by six kinds of parts, that is, the lower casing 12, the upper casing 13, the knob 14, the pair of metal clip opening spring members 21, the spring 56, and the fastening band 63. It is therefore possible to reduce the parts in number in comparison with the conventional clip driver. Each of the lower casing 12, the upper casing 13, and the knob 14 can be integrally formed and therefore can be easily produced through injection molding or the like. Further, such assembling as described above can be extremely easily performed without using any special tool.

When documents are to be bound together by the clip, the clip 1 is inserted from the clip insertion inlet 42 with the guide portion 5 of the clip 1 made frontward. Although the longitudinal size of the clip insertion inlet 42 is narrower than that of the bent portion 2 of the clip 1 because of provision of the cover portion 44, the cover portion 44 can be lifted by insertion of the clip 1 so that the clip 1 can be inserted with small force. The lug portions 4 sideward projected from the opposite sides of the clip 1 are mounted on the lug guide step portions 28 of the lower casing 12 respectively and the bent portion 2 of the clip 1 rests on the bottom portion of the groove 24. If the clip driver 11 is inclined with the insertion inlet 17 made lower after one or a plurality of clips 1 have been accommodated in the groove 24 in a manner as described above, the bent portion 2 of the head clip 1 at the head of the clips is inserted into the front end groove 26, and at the same time, the lug portions 4 of the same clip 1 are positioned on the engagement step portions 34 respectively. Thus, the clip 1 at the head is in a lowered position. The location of the clip 1 in such a lowered position is to bring the guide portions 5 of clip 1 to the vertexes of the clip opening spring members 21 respectively. In this location, the vertexes of the clip opening spring members 21 are inserted into the space between the guide portions 5, and stop when the vertexes abut on the abutment portions of the two grasping portions 3. The height of the engagement step portions 34 is therefore adjusted in advance so that the vertexes of the clip opening spring members 21 are even in level to the space between the guide portions 5 of the clip 1.

After documents or the like have been inserted into the insertion inlet 17, the clip driver 11 is held by one hand with a forefinger put in the recess portion 36 and with a thumb put on the knob projection portion 51 of the knob 14, and then the knob projection portion 51 is pushed down by the thumb. As a result, the front end push-out portion 52 and the knob projection portion 51 of the knob 14 supported substantially horizontally by the spring 56 are lowered so that the lower end surfaces of the opposite side portions 54 of the knob projection portion 51 abut on the upper surfaces of the guide rims 43. With this state kept, the knob 14 is slid toward the insertion inlet 17. As a result, the front end of the push-out portion 52 abuts on the bent portion 2 of the head clip 1. Then, if the knob 14 is slid frontward against the spring force of the spring 56, the clip 1 is advanced by the knob 14 so that the vertexes of the clip opening spring members 21 are inserted into the space of the guide portions 5 to open it. When the extremities of the guide portions 5 are located at the insertion inlet 17, the pair of grasping portions 3 are opened substantially in parallel to each other so that the documents or the like can be inserted therebetween. If the knob 14 is further advanced, the engagement between the clip opening spring members 21 and the guide portions 5 of the clip 1 is released, and the clip 1 can be ejected from the insertion inlet 17. Thus, the clip 1 grasps the documents or the like between the grasping portions 3. The maximum thickness of documents which can be clipped together is substantially equal to the thickness or height of the bent portion 2 of the clip 1.

When the next clip 1 is disposed at the head position, the knob 14 is released from the finger and the clip driver 11 is inclined so as to make the insertion inlet 17 on the front end of the clip driver 11 a little lower than the horizontal level so that the next clip comes into the recess 25. That is, the push-out portion 52 of the knob 14 is returned to the upper original position by the function of the spring 56 when the knob 14 is released from the finger, and the lower surface of the push-out portion 52 is not projected into the path of the clip 1 formed by the lower and upper casings 12 and 13, and therefore the clip 1 can be freely slid into the groove 24.

Although the present invention has been described with reference to the preferred embodiment, it will be appreciated that the description has made for the purpose of understanding of the present invention, and various changes and modifications can be made without departing from the spirit and scope of the appended claims.

What is claimed is:

1. A clip driver for binding documents or the like together by using a clip formed from a single elastic plate-like member and constituted by a bent portion and a pair of grasping portions continued from said bent portion, said grasping portions having extremities normally contacting with each other so as to grasp said documents or the like between said grasping portions, said clip driver comprising:

a lower casing having at its front end a lower opening portion forming part of an insertion inlet for said documents or the like, said lower casing having an upper surface on which at least one said clip is mounted with said grasping portions made directed toward said insertion inlet so that said clip is slidable in a longitudinal direction of said clip driver;

an upper casing having at its front end an upper opening portion forming said insertion inlet together with said lower opening portion of said lower casing and having at its rear end a clip insertion inlet for inserting said clip;

a knob mounted in a rectangular opening which is formed in said upper casing at its front end side so as to extend in said longitudinal direction, said knob being slidable in said longitudinal direction and being movable up and down within a predetermined range, said knob having a knob projection portion projected upward from said opening, a push-out portion formed on a front end of said knob projection portion so that said push-out portion comes to abut on said bent portion of said clip when said knob is lowered, and a projection portion rearward extending from a rear end of said knob projection portion;

clip opening spring members provided in said insertion inlet formed by said lower and upper casings for opening said grasping portions of said clip in the directions opposite to each other; and an elastic member provided with its opposite ends attached to said projection portion and to a lower surface portion of said upper casing so that said knob is normally biased toward a rear end of said clip driver and at the same time said push-out portion is biased upward.

2. A clip driver according to claim 1, in which a substantially horizontally-projected projection portion is formed on a rear end surface of said lower casing and an engagement portion to be engaged with said projection portion is formed on a rear end portion of said upper casing so that said lower and upper casings are assembled in the condition that said engagement portion engages with said projection portion, the assembly of said lower and upper casings being fixed by means of a fastening band at an outer periphery thereof on said insertion inlet side.

3. A clip driver according to claim 1, in which end portions of said clip opening spring members at the side opposite to said insertion inlet are located between said pair of grasping portions of the clip mounted in said lower casing so that said clip at the insertion inlet is restricted so as not to come off by itself from said insertion inlet.

4. A clip driver according to claim 1, in which substantially horizontally sideward projected and longitudinally extending rim portions are provided on the opposite side surfaces of said opening of said upper casing, and in which said push-out portion of said knob has first lower projections formed on a lower surface thereof so as to engage with lower surfaces of said rim portions respectively when said knob is moved up, said projection portion of said knob has second lower projections formed on a lower surface thereof so as to engage with said lower surfaces of said rim portions respectively, and said knob projection portion of said knob has upper projections formed on opposite sides thereof for limiting downward movement of said knob, so that said knob is supported by said first lower projections, said second lower projections, and said upper projections so as to be slidable without coming off.

5. A clip driver according to claim 1, in which a limitation portion is formed on a lower surface at a rear end of said upper casing so as to abut on said projection portion of said knob to thereby limit retreating of said knob, and in which a rear end of said projection portion is tapered so as to point-contact with said limitation portion, said point-contact portion being positioned lower than the attachment portion of said elastic member.

6. A clip driver according to claim 1, in which an engagement portion to be engaged with said bent portion of said clip is formed on a front end of said projection portion of said knob.

7. A clip driver according to claim 1, in which a cover portion is formed so as to rearward extend from a front end of said clip insertion inlet of said upper casing, said cover portion being formed so as to have elasticity so that said cover portion is able to be biased vertically, said cover portion being positioned so that a gap slightly narrower than a thickness of said bent portion of said clip is formed between a free end of said cover portion and a rear end of said clip insertion inlet.

* * * * *